US009932566B2

(12) United States Patent
Kennedy et al.

(10) Patent No.: US 9,932,566 B2
(45) Date of Patent: Apr. 3, 2018

(54) CIS-BLOCKED GUIDE RNA

(71) Applicant: Agilent Technologies, Inc., Santa Clara, CA (US)

(72) Inventors: Andrew Kennedy, Sunnyvale, CA (US); Daniel E. Ryan, San Francisco, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 0 days.

(21) Appl. No.: 14/820,521

(22) Filed: Aug. 6, 2015

(65) Prior Publication Data
US 2016/0040189 A1    Feb. 11, 2016

Related U.S. Application Data

(60) Provisional application No. 62/034,237, filed on Aug. 7, 2014, provisional application No. 62/076,226, filed on Nov. 6, 2014.

(51) Int. Cl.
*C12N 15/00*   (2006.01)
*C12N 9/22*    (2006.01)
*C12N 15/90*   (2006.01)
*C12N 15/10*   (2006.01)
*C12N 15/113*  (2010.01)

(52) U.S. Cl.
CPC ............ *C12N 9/22* (2013.01); *C12N 15/102* (2013.01); *C12N 15/113* (2013.01); *C12N 15/902* (2013.01); *C12N 2310/20* (2017.05); *C12Y 301/04* (2013.01)

(58) Field of Classification Search
CPC ...... C12N 9/22; C12N 15/902; C12N 15/102; C12N 15/113; C12N 2310/20; C12Y 301/04
See application file for complete search history.

(56) References Cited

U.S. PATENT DOCUMENTS

| | | |
|---|---|---|
| 2014/0170753 A1 | 6/2014 | Zhang |
| 2014/0273226 A1 | 9/2014 | Wu |
| 2014/0273233 A1 | 9/2014 | Fuqiang et al. |
| 2015/0071900 A1* | 3/2015 | Liu ...................... C12N 15/115 424/94.3 |

FOREIGN PATENT DOCUMENTS

| | | | |
|---|---|---|---|
| CN | 103388006 A | 11/2013 | |
| WO | 89/02439 A1 | 3/1989 | |
| WO | 95/06731 A2 | 3/1995 | |
| WO | 95/11910 A1 | 5/1995 | |
| WO | 2013/176772 A1 | 11/2013 | |
| WO | WO 2013/176772 | * 11/2013 | ............ C07K 19/00 |
| WO | 2014/144592 A2 | 9/2014 | |
| WO | 2014/144761 A2 | 9/2014 | |

OTHER PUBLICATIONS

Carroll, Staying on target with CRISPR-Cas. Nat. Biotechnol., 31, 807-9 (2013).

(Continued)

*Primary Examiner* — Reza Ghafoorian

(57) ABSTRACT

This invention discloses reagents and methods for increasing specificity and efficiency of RNA-guided genome editing.

19 Claims, 3 Drawing Sheets

(56) References Cited

OTHER PUBLICATIONS

Cong et al., Science 339 (6121): 819-823 (2012).
Cho et al., Nature Biotechnology 31, 230-232 (2013).
Mojica et al., Microbiology. Mar. 2009;155(Pt 3):733-40.
Kleinstiver et al., "Engineered CRISPR-Cas9 nucleases with altered PAM specificities", Nature 523,481-485 (2015).
Ran et al., "In vivo genome editing using *Staphylococcus aureus* Cas9", Nature 520,186-191 (2015).
Ran et al., Double nicking by RNA-guided CRISPR Cas9 for enhanced genome editing specificity. Cell, 154, 1380-9 (2013).
Mali et al., RNA-guided human genome engineering via Cas9. Science, 339, 823-6 (2013).
Tsai et al., Dimeric CRISPR RNA-guided FokI nucleases for highly specific genome editing. Nat. Biotechnol., 32, 569-76 (2014).
Fu et al., Improving CRISPR-Cas nuclease specificity using truncated guide RNAs. Nat. Biotechnol., 32, 279-84 (2014).
Mali et al. CAS9 transcriptional activators for target specificity screening and paired nickases for cooperative genome engineering. Nat. Biotechnol., 31, 833-8 (2013).
Jinek et al., A programmable dual-RNA-guided DNA endonuclease in adaptive bacterial immunity. Science, 337, 816-21 (2012).
Gasiunas et al., Proc Natl Acad Sci USA. Sep. 25, 2012; 109(39): E2579-E2586.
Hou et al., Proc Natl Acad Sci U S A. Sep. 24, 2013;110(39):15644-9.
www.addgene.org/CRISPR/ (printed Aug. 6, 2015).
International Search Report and Written Opinion for related PCT/US2015/044111 dated Oct. 19, 2015.
Kennedy, Andrew B. et al., 'A versatile cis-blocking and trans-activation strategy for ribozyme characterization', Nucleic Acids Research, Epub. Nov. 15, 2012, vol. 41, No. 2, e41 (pp. 1-13).
Wu, Xuebing et al., 'Target specificity of the CRISPR-Cas9 system', Quantitive Biology, Jun. 2014, vol. 2, No. 2, pp. 59-70.
Qi, Lei S. et al., 'Repurposing CRISPR as an RNA-guided platform for sequence-specific control of gene expression', Cell, Feb. 28, 2013, vol. 152, No. 5, pp. 1173-1183.

\* cited by examiner

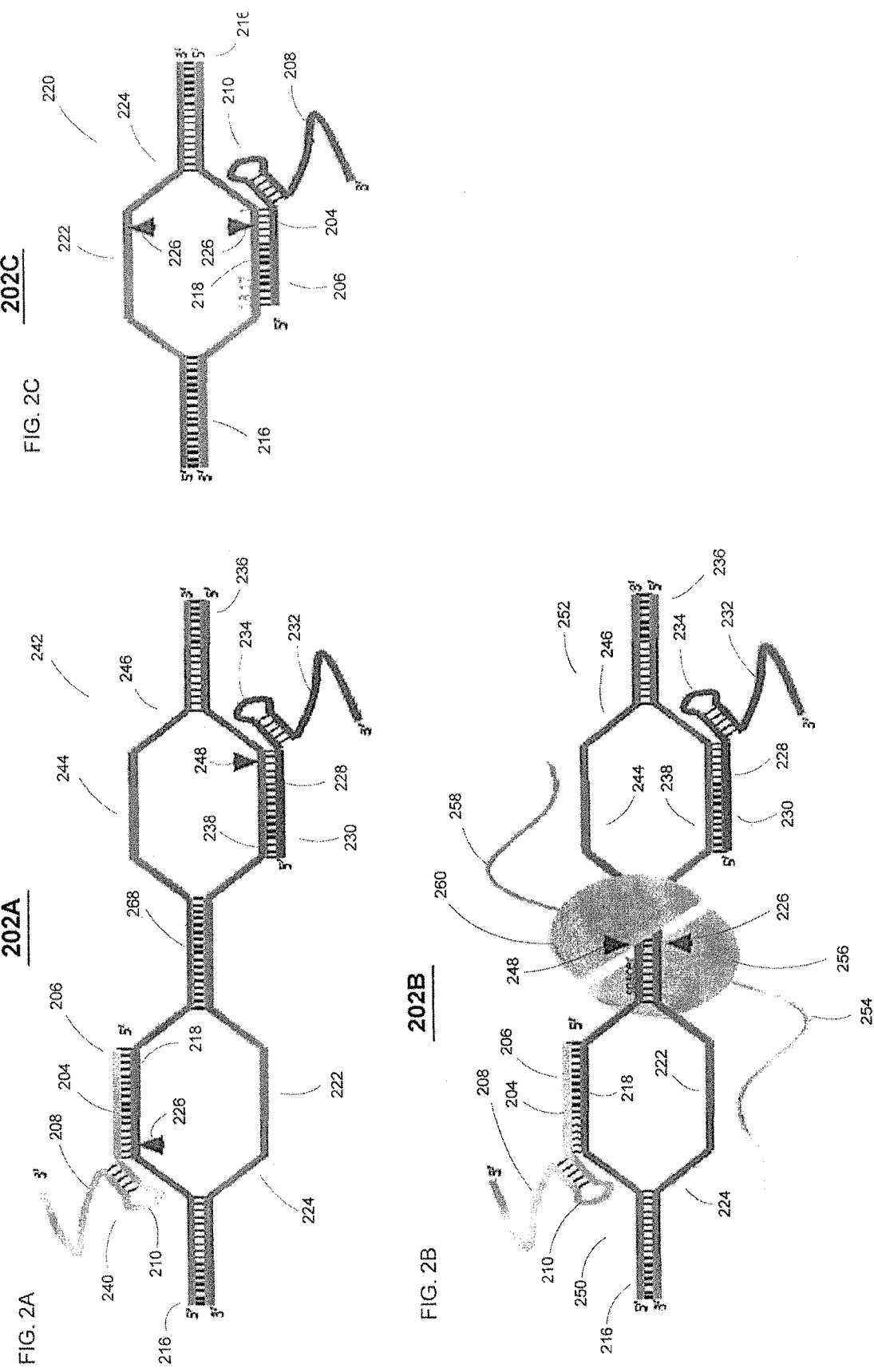

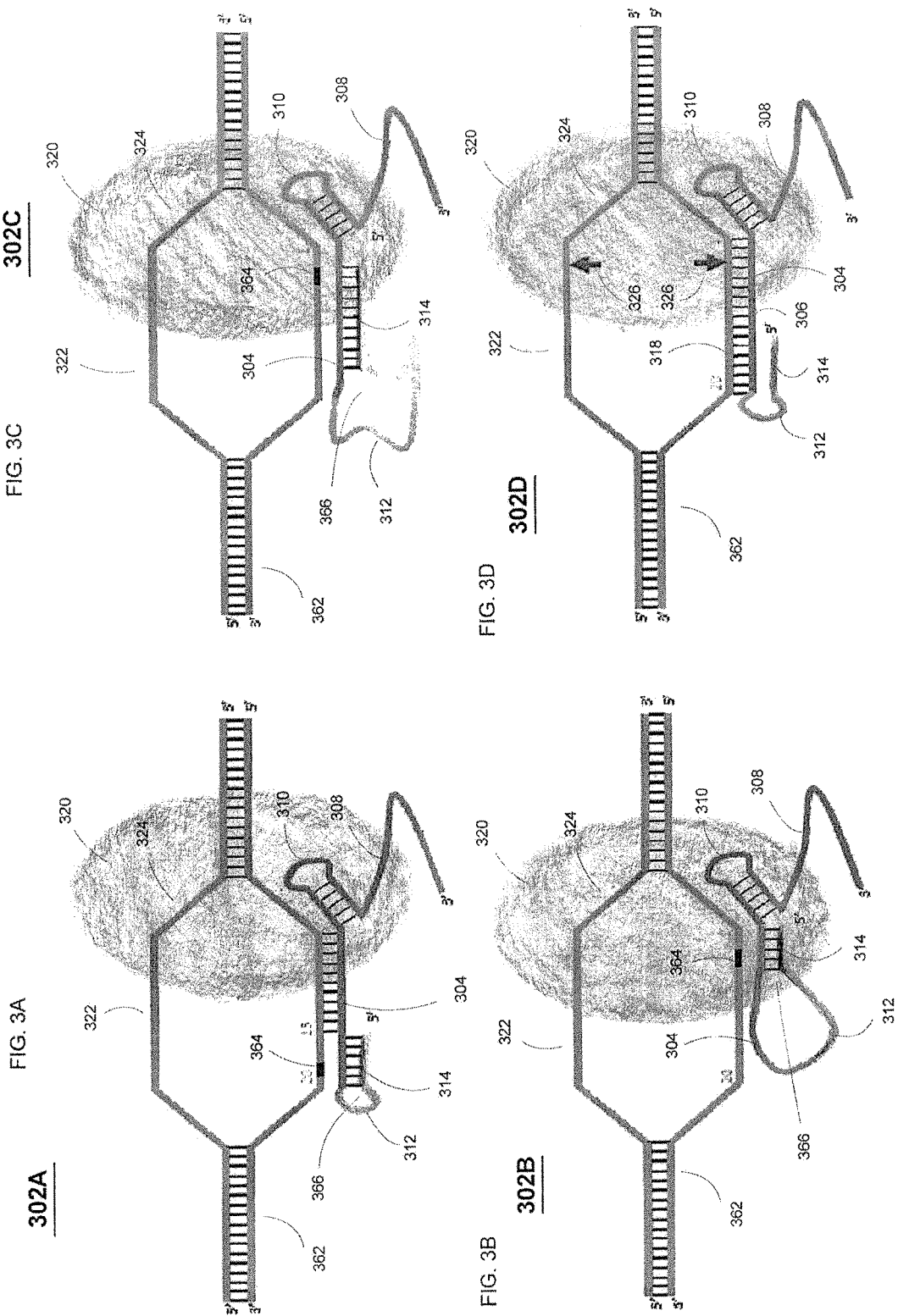

SEQUENCE LISTING

<160> NUMBER OF SEQ ID NOS: 9

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

-continued

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

```
            785                 790                 795                 800
     Val Glu Asn Thr Gln Leu Gln Asn Gly Lys Leu Tyr Leu Tyr Tyr Leu
                         805                 810                 815
     Gln Asn Gly Arg Asp Met Tyr Val Asp Gln Glu Leu Asp Ile Asn Arg
                 820                 825                 830
     Leu Ser Asp Tyr Asp Val Asp His Ile Val Pro Gln Ser Phe Leu Lys
                 835                 840                 845
     Asp Asp Ser Ile Asp Asn Lys Val Leu Thr Arg Ser Asp Lys Asn Arg
         850                 855                 860
     Gly Lys Ser Asp Asn Val Pro Ser Glu Glu Val Val Lys Lys Met Lys
     865                 870                 875                 880
     Asn Tyr Trp Arg Gln Leu Leu Asn Ala Lys Leu Ile Thr Gln Arg Lys
                         885                 890                 895
     Phe Asp Asn Leu Thr Lys Ala Glu Arg Gly Gly Leu Ser Glu Leu Asp
                     900                 905                 910
     Lys Ala Gly Phe Ile Lys Arg Gln Leu Val Glu Thr Arg Gln Ile Thr
                 915                 920                 925
     Lys His Val Ala Gln Ile Leu Asp Ser Arg Met Asn Thr Lys Tyr Asp
             930                 935                 940
     Glu Asn Asp Lys Leu Ile Arg Glu Val Lys Val Ile Thr Leu Lys Ser
     945                 950                 955                 960
     Lys Leu Val Ser Asp Phe Arg Lys Asp Phe Gln Phe Tyr Lys Val Arg
                         965                 970                 975
     Glu Ile Asn Asn Tyr His His Ala His Asp Ala Tyr Leu Asn Ala Val
                     980                 985                 990
     Val Gly Thr Ala Leu Ile Lys Lys  Tyr Pro Lys Leu Glu  Ser Glu Phe
                 995                 1000                1005
     Val Tyr  Gly Asp Tyr Lys Val  Tyr Asp Val Arg Lys  Met Ile Ala
         1010                1015                 1020
     Lys Ser  Glu Gln Glu Ile Gly  Lys Ala Thr Ala Lys  Tyr Phe Phe
         1025                1030                 1035
     Tyr Ser  Asn Ile Met Asn Phe  Phe Lys Thr Glu Ile  Thr Leu Ala
         1040                1045                 1050
     Asn Gly  Glu Ile Arg Lys Arg  Pro Leu Ile Glu Thr  Asn Gly Glu
         1055                1060                 1065
     Thr Gly  Glu Ile Val Trp Asp  Lys Gly Arg Asp Phe  Ala Thr Val
         1070                1075                 1080
     Arg Lys  Val Leu Ser Met Pro  Gln Val Asn Ile Val  Lys Lys Thr
         1085                1090                 1095
     Glu Val  Gln Thr Gly Gly Phe  Ser Lys Glu Ser Ile  Leu Pro Lys
         1100                1105                 1110
     Arg Asn  Ser Asp Lys Leu Ile  Ala Arg Lys Lys Asp  Trp Asp Pro
         1115                1120                 1125
     Lys Lys  Tyr Gly Gly Phe Asp  Ser Pro Thr Val Ala  Tyr Ser Val
         1130                1135                 1140
     Leu Val  Val Ala Lys Val Glu  Lys Gly Lys Ser Lys  Lys Leu Lys
         1145                1150                 1155
     Ser Val  Lys Glu Leu Leu Gly  Ile Thr Ile Met Glu  Arg Ser Ser
         1160                1165                 1170
     Phe Glu  Lys Asn Pro Ile Asp  Phe Leu Glu Ala Lys  Gly Tyr Lys
         1175                1180                 1185
     Glu Val  Lys Lys Asp Leu Ile  Ile Lys Leu Pro Lys  Tyr Ser Leu
         1190                1195                 1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(20)
<223> OTHER INFORMATION: n is a, c, g, t or u
<300> PUBLICATION INFORMATION:
<301> AUTHORS: Chen B, Gilbert LA, Cimini BA, Schnitzbauer J, Zhang W,
      Li GW, Park J, Blackburn EH, Weissman JS, Qi LS, Huang B
<302> TITLE: Dynamic imaging of genomic loci in living human cells by an
      optimized CRISPR/Cas system
<303> JOURNAL: Cell
<304> VOLUME: 155
<305> ISSUE: 7
<306> PAGES: 1479-91
<307> DATE: 2013-12-19

<400> SEQUENCE: 2
nnnnnnnnnn nnnnnnnnnn guuuaagagc uaugcuggaa acagcauagc aaguuuaaau    60
aaggcuaguc cguuaucaac uugaaaaagu ggcaccgagu cggugcuuuu uuu           113

<210> SEQ ID NO 3
<211> LENGTH: 79
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaaccauuc aaaacagcau agcaaguuaa aauaaggcua guccguuauc aacuugaaaa    60
aguggcaccg agucggugc                                                 79
```

```
<210> SEQ ID NO 4
<211> LENGTH: 60
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uagcaaguua aaauaaggcu aguccguuau caacuugaaa aaguggcacc gagucggugc    60

<210> SEQ ID NO 5
<211> LENGTH: 64
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
agcauagcaa guuaaaauaa ggcuaguccg uuaucaacuu gaaaaagugg caccgagucg    60
gugc                                                                64

<210> SEQ ID NO 6
<211> LENGTH: 70
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
caaaacagca uagcaaguua aaauaaggcu aguccguuau caacuugaaa aaguggcacc    60
gagucggugc                                                          70

<210> SEQ ID NO 7
<211> LENGTH: 45
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
uagcaaguua aaauaaggcu aguccguuau caacuugaaa aagug                    45

<210> SEQ ID NO 8
<211> LENGTH: 32
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uagcaaguua aaauaaggcu aguccguuau ca                                  32

<210> SEQ ID NO 9
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 9
uagcaaguua aaauaaggcu aguccg                                            26
```

CIS-BLOCKED GUIDE RNA

CROSS-REFERENCE TO RELATED APPLICATIONS

This application claims the benefit of priority from U.S. Provisional Application No. 62/034,237, filed on Aug. 7, 2014 and U.S. Provisional Application No. 62/076,226, filed on Nov. 6, 2014, the entire content of each of which is incorporated herein by reference in its entirety.

FIELD OF THE INVENTION

This invention relates to reagents and methods for increasing specificity and efficiency of RNA-guided genome editing, such as that mediated by the CRISPR-Cas system.

BACKGROUND OF THE INVENTION

Genome editing is a powerful technology for genetic manipulation and modification. A recently developed genome modification technology utilizes the bacterial clusters of regularly interspaced short palindromic repeats (CRISPR) associated protein 9 (Cas9), an RNA-guided DNA endonuclease, to induce a specific double-stranded break (DSB) at DNA target sites comprising a 3-nucleotide (nt) protospacer adjacent motif (PAM) and a 20-bp sequence complementary, to the 5' end of a CRISPR guide RNA (gRNA) bound by Cas9. The guide RNA-Cas9 complex identifies and base pairs with its cognate DNA target sequence, resulting in target cleavage to form a DSB (FIG. 1). It has been observed that the CRISPR-Cas9 system tolerates a limited extent of base-pair mismatching between the DNA substrate and the 20-nt guide sequence of the guide RNA, which results in undesired off-target DNA cleavages (Carroll, D. (2013) *Nat. Biotechnol.,* 31, 807-9).

As formation of off-target mutations is of profound concern to developers of genome editing technologies, three different strategies have been devised to improve the specificity of CRISPR-Cas9 genome modification (FIGS. 2A-2C). These strategies all reduce, but do not abolish, off-target DNA cleavage at a cost of diminishing the on-target cleavage activity with respect to the comparable unmodified CRISPR:Cas9 guided nuclease system.

The first strategy involves a Cas9 mutant (Cas9n; also known as Cas9-D10A) that cleaves and nicks just one strand of the target DNA. Two distinct guide RNA sequences are designed such that Cas9n creates offset nicks on opposite strands, thereby creating a DSB in the DNA target region (FIG. 2A). A variation of this strategy uses two different Cas9 mutants, each recognizing one of the two strands. Compared to the unmodified CRISPR-Cas9 system, this double nickase strategy requires two adjacent targetable DNA sequences and has lower on-target modification activity (Ran et al. (2013) *Cell,* 154, 1380-9). Additionally, although specificity is increased, there is still significant off-target activity, and single-stranded DNA nicks are weakly mutagenic (Mali et al., (2013) *Science,* 339, 823-6).

A second strategy employs cleavage-deactivated Cas9 (dCas9) fused to a dimeric-dependent FokI nuclease domain (FokI-dCas9) with two distinct guide RNAs specifying the DNA target site (FIG. 2B). Although this strategy demonstrated greater specificity than that of the paired nickase strategy, it showed further reduction in on-target cleavage efficiency as compared to the original CRISPR-Cas9 nuclease system using one or the other guide RNA of each pair (Tsai et al., (2014) *Nat. Biotechnol.,* 32, 569-76). Additionally, as with the paired nickase strategy, the FokI-dependent approach is limited by its requirement for two adjacent targetable DNA sequences, potentially restricting its utility and versatility in genome modification applications.

In a third strategy, improvement in the specificity of CRISPR-Cas9 cleavage was achieved by truncating the 20-nt guide sequence by 2 or 3 nucleotides at its 5' end to generate truncated guide RNAs (tru-RGNs, Fu et al., (2014) *Nat. Biotechnol.,* 32, 279-84). Comparing the DNA cleavage activity of full-length guide RNA and tru-RGNs targeting a few different genomic sequences, it was demonstrated that off-target cleavage activity can be reduced with tru-RGNs. However, for some DNA target sequences, off-target activities of tru-RGNs were still significant and even elevated in one instance relative to off-target activities of Cas9 complexed with full-length guide RNA. Additional truncation of the 5' end generally reduces on-target guide RNA-Cas9 activity, reducing it to background levels when the DNA-pairing sequence is truncated to 15 nt or shorter.

Thus, there is a need for reagents and methods for increasing specificity and efficiency of RNA-guided genome editing.

BRIEF DESCRIPTION OF THE DRAWINGS

FIGS. 2A-2C are a set of diagrams showing conventional strategies to improve Cas9-mediated cleavage specificity. (A) The paired nickase strategy uses two copies of a Cas9 mutant (Cas9-D10A) to make offset single-stranded nicks at two DNA target sites directed by two distinct guide RNA sequences. (B) The dimeric RNA-guided FokI nuclease strategy fuses a catalytically inactive Cas9 protein (dCas9) to a dimerization-dependent FokI nuclease domain. Two guide RNAs direct the dCas9-FokI fusion proteins to dimerize and cleave both strands of DNA at the target site. (C) The truncated guide RNA approach removes 2-3 nt from the 5' end of the guide RNA but does not modify the Cas9 protein.

FIGS. 3A-3D are a set of diagrams showing an exemplary cis-blocked guide RNA strategy for improving Cas9-mediated DNA cleavage specificity and efficiency, where a linker-tethered blocking sequence hybridizes with and sequesters a portion of the DNA-binding region of the guide RNA, and the resulting cis-blocked stem thwarts base pairing of guide RNA with off-target DNA sequences (black lines). The blocking sequence can be designed to hybridize with the 5' end (A) or the 3' end (B) of the 20-nt DNA-binding region and with different lengths (FIGS. 3A, 3B, and 3C). In the presence of a cognate DNA target (FIG. 3D), Cas9 can unwind the cis-blocked stem as the DNA target strand hybridizes with the guide RNA, resulting in hybridization of the full 20 nt between guide RNA and target DNA, and leading to maximal Cas9 cleavage efficiency.

DETAILED DESCRIPTION OF THE INVENTION

Figure 1:
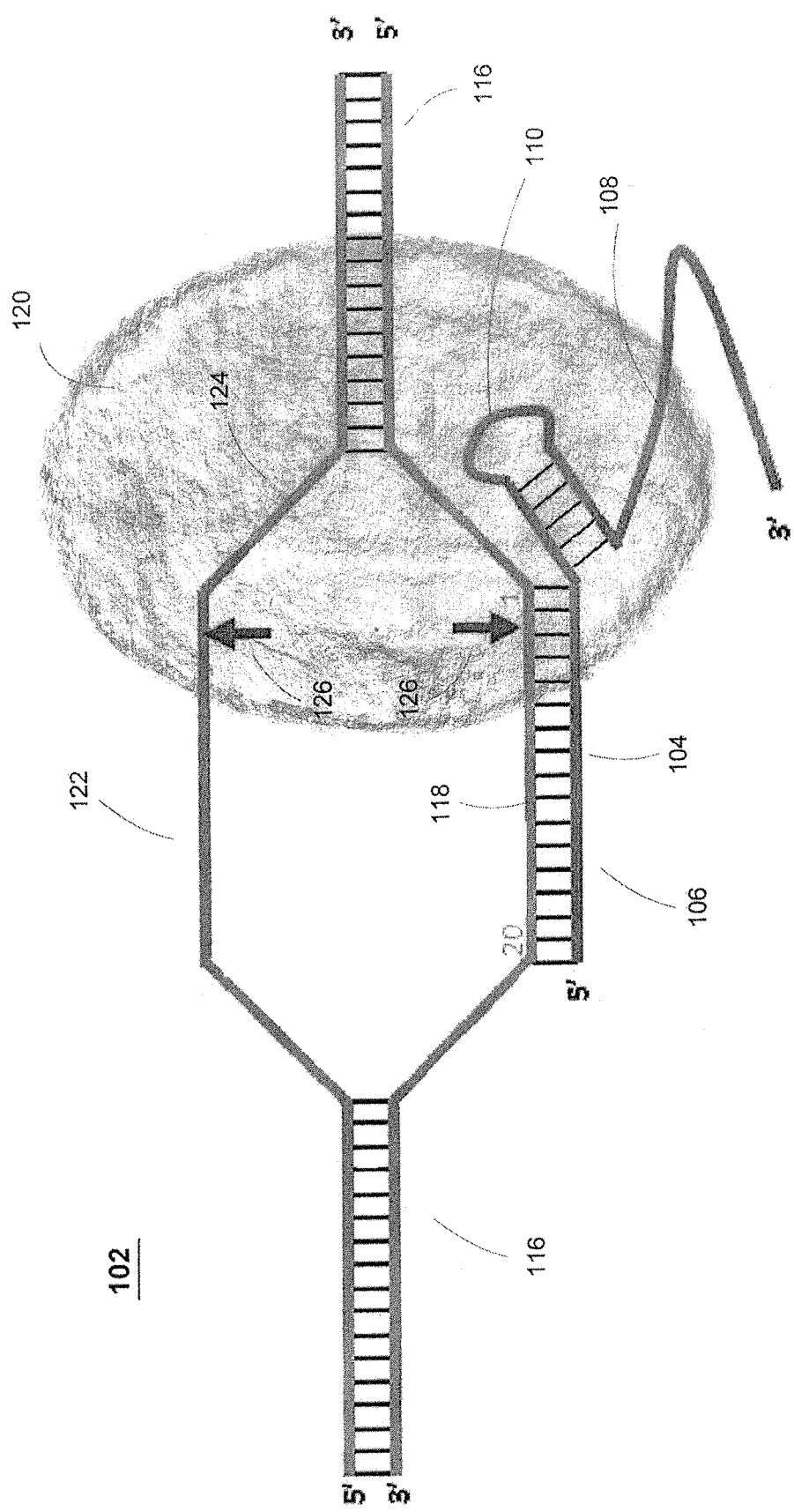
FIG. 1 is a diagram showing an example of CRISPR-Cas9-mediated sequence-specific cleavage of DNA.

This invention is based, at least in part, on an unexpected discovery that highly specific and efficient RNA-guided genome editing could be achieved using Cas-guide RNAs that contain engineered blocking sequences and modifiers.

I. Definitions

A nucleic acid refers to a DNA molecule (for example, but not limited to, a cDNA or genomic DNA) or an RNA molecule (for example, but not limited to, an mRNA), and includes DNA or RNA analogs. A DNA or RNA analog can be synthesized from nucleotide analogs. The DNA or RNA molecules may include portions that are not naturally occurring, such as modified bases, modified backbone, deoxyribonucleotides in an RNA, etc. The nucleic acid molecule can be single-stranded or double-stranded.

The term "isolated" when referring to nucleic acid molecules or polypeptides means that the nucleic acid molecule or the polypeptide is substantially free from at least one other component with which it is associated or found together in nature.

As used herein, the term "target nucleic acid" or "target" refers to a nucleic acid containing a target nucleic acid sequence. A target nucleic acid may be single-stranded or double-stranded, and often is double-stranded DNA. A "target nucleic acid sequence," "target sequence" or "target region," as used herein, means a specific sequence or the complement thereof that one wishes to bind to or nick/cleave using a CRISPR system. A target sequence may be within a nucleic acid in vitro or in vivo within the genome of a cell, which may be any form of single-stranded or double-stranded nucleic acid.

A "target nucleic acid strand" refers to a strand of a target nucleic acid that is subject to base-pairing with a guide RNA as disclosed herein. That is, the strand of a target nucleic acid that hybridizes with the crRNA and guide sequence is referred to as the "target nucleic acid strand." The other strand of the target nucleic acid, which is not complementary to the guide sequence, is referred to as the "non-complementary strand." One skilled in the art could appreciate that such a "non-complementary strand" corresponds to the top strand shown in FIGS. 3A-D. In the case of double-stranded target nucleic acid (e.g., DNA), each strand can be a "target nucleic acid strand" to design crRNA and guide RNAs and used to practice the methods of this invention as long as there is a suitable PAM site.

"Hybridization" or "hybridizing" refers to a process where completely or partially complementary nucleic acid strands come together under specified hybridization conditions to form a double-stranded structure or region in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

By "cleavage" it is meant the breakage of the covalent backbone of a DNA molecule. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, a complex comprising a guide RNA and a Cas variant is used for targeted single-stranded DNA cleavage, i.e., nicking.

By "nuclease domain" of a nuclease it is meant the polypeptide sequence or domain within the nuclease which possesses the catalytic activity for DNA cleavage. A cleavage domain can be contained in a single polypeptide chain or cleavage activity can result from the association of two (or more) polypeptides. A single nuclease domain may consist of more than one isolated stretch of amino acids within a given polypeptide.

A "Cas9 mutant" or "Cas9 variant" refers to a protein or polypeptide derivative of the wild type S. pyogenes Cas9 protein (i.e., SEQ ID NO: 1), e.g., a protein having one or more point mutations, insertions, deletions, truncations, a fusion protein, or a combination thereof. It retains substantially one or more of the nuclease, RNA binding, or DNA targeting activities of the Cas9 protein. The protein or polypeptide can comprise, consist of, or consist essentially of a fragment of SEQ ID NO: 1. In general, the mutant or variant is at least 50% (e.g., any number between 50% and 100%, inclusive, including but not limited to at least 55%, at least 60%, at least 65%, at least 70%, at least 75%, at least 80%, at least 85%, at least 90%, at least 95%, at least 98%, and at least 99%) identical to SEQ ID NO: 1. The mutant or variant can bind to an RNA molecule and be targeted to a specific DNA sequence via the RNA molecule, and may additionally have a nuclease activity. Examples of these domains include RuvC like motifs (aa. 7-22, 759-766 and 982-989 in SEQ ID NO: 1) and HNH motif (aa 837-863). See Gasiunas et al., Proc Natl Acad Sci USA. 2012 Sep. 25; 109(39): E2579-E2586 and WO2013176772.

A nuclease or a nuclease mutant or variant (e.g., a Cas9 mutant or variant) "having a single-strand nicking activity" refers to a nuclease or a nuclease mutant or variant that has reduced ability to cleave one of two strands of a dsDNA as compared to that to cleave the other strand. For example, the nuclease or a nuclease mutant or variant can have a mutation (e.g., amino acid substitution) that reduces the function of the RuvC domain (or the HNH domain) and as a result reduces the ability to cleave one strand of the target DNA. Examples of such variant include the D10A and H840A Cas9 variants (or variants with another amino acid substitution at position D10 and/or H840), and Cas enzymes for other species with the same substitution at equivalent site.

As used herein, the term "guide RNA" generally refers to an RNA molecule (or a group of RNA molecules collectively) that can bind to a CRISPR protein and target the CRISPR protein to a specific location within a target DNA. A guide RNA can comprise two segments: a DNA-targeting guide segment and a protein-binding segment. The DNA-targeting segment comprises a nucleotide sequence that is complementary to (or at least can hybridize to under stringent conditions) a target sequence. The protein-binding segment interacts with a CRISPR protein, such as a Cas9 or Cas9 related polypeptide. These two segments can be located in the same RNA molecule or in two or more separate RNA molecules. When the two segments are in separate RNA molecules, the molecule comprising the DNA-targeting guide segment is sometimes referred to as the guide RNA, while the molecule comprising the protein-binding segment is referred to as the tracrRNA.

As used herein, the term "portion" or "fragment" of a sequence refers to any portion of the sequence (e.g., a nucleotide subsequence or an amino acid subsequence) that is smaller than the complete sequence. Portions of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length. The 5' portion of a sequence is located within the 5' one-third of the sequence, the 3' portion is located within the 3' one-third, and the middle portion is within the middle one-third.

As used herein, the term "contacting," when used in reference to any set of components, includes any process whereby the components to be contacted are mixed into same mixture (for example, are added into the same compartment or solution), and does not necessarily require actual physical contact between the recited components. The recited components can be contacted in any order or any combination (or sub-combination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting" a target nucleic acid or a cell with one or more reaction components, such as an Cas protein or guide RNA, includes any or all of the following situations: (i) the target or cell is contacted with a first component of a reaction mixture to create a mixture; then other components of the reaction mixture are added in any order or combination to the mixture; and (ii) the reaction mixture is fully formed prior to mixture with the target or cell.

The term "mixture" as used herein, refers to a combination of components, that are interspersed and not in any particular order. Examples of mixtures of elements include a number of different components that are dissolved in the same aqueous solution, or a number of different components attached to a solid support at random or in no particular order in which the different components are not spatially distinct.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

II. CRISPR-Cas System

The CRISPR-Cas system is a class of nucleic acid targeting system originally discovered in prokaryotes that somewhat resemble siRNA/miRNA systems found in eukaryotes. The system consists of an array of short repeats with intervening variable sequences of constant length (i.e., clusters of regularly interspaced short palindromic repeats, or CRISPRs) and CRISPR-associated (Cas) proteins. In CRISPR, each repetition contains a series of base pairs followed by the same or a similar series in reverse and then by 30 or so base pairs known as "spacer DNA."

The spacers are short segments of DNA from a virus or a plasmid, which have been removed from the virus or plasmid and incorporated into the host genome between the short repeat sequences, and serve as a "memory" of past exposures. The RNA of the transcribed CRISPR arrays is processed by a subset of the Cas proteins into small guide RNAs (which generally have two components as discussed below) containing the viral or plasmid sequences, which direct Cas-mediated cleavage of viral or plasmid nucleic acid sequences that contain so-called protospacer adjacent motif (PAM) site and correspond to the small guide RNAs. The CRISPR-Cas system functions as a prokaryotic immune system, as the spacers recognize and silence exogenous genetic elements in a manner analogous to RNAi in eukaryotic organisms thereby conferring resistance to exogenous genetic elements such as plasmids and phages.

A functional bacterial CRISPR-Cas system requires three components: the Cas protein which provides the nuclease activity and two short, non-coding RNA species referred to as CRISPR RNA (crRNAs) and trans-acting RNA (tracrRNA), which two RNA species form the above-mentioned guide RNA. Type II CRISPR is one of the most well characterized systems and carries out targeted DNA double-strand break in four sequential steps. First, two non-coding RNAs, a pre-crRNA and a tracrRNA, are transcribed from the CRISPR locus. Second, the tracrRNA hybridizes to the repeat regions of the pre-crRNA molecules and mediates processing of pre-crRNA molecules into mature crRNA molecules containing individual spacer sequences. Third, a mature crRNA:tracrRNA complex directs the Cas nuclease to target DNA via Wastson-Crick base-pairing between the spacer on the crRNA and the complement of the protospacer sequence on the target DNA next to a PAM. Finally, the Cas nuclease mediates cleavage of the target DNA to create a double-stranded break within the target site.

Shown in FIG. 1 is a diagram of CRISPR-Cas9-mediated sequence-specific cleavage of DNA by a CRISPR-Cas9 system 102. The guide RNA 104 is depicted as an engineered single-guide RNA with a 20-nt guide sequence at the 5' end 106, which is complementary to a 20-bp target sequence 118 (where 1 and 20 in FIG. 1 represent the beginning and end of the target sequence) in DNA, and a 3' domain 108 (corresponding to the tracrRNA) that binds a Cas9 nuclease 120. The 5' domain 106 has crRNA activity, and the 3' domain 108 has tracrRNA activity. The single-guide RNA comprises a hairpin or duplex structure 110 between the 5' and 3' domains. The Cas9:guide RNA complex binds and cleaves a target DNA sequence 116 containing a protospacer 122 directly upstream of a 3-nt PAM site 124. Both strands of the target DNA are cleaved by Cas9 at the sites 126 indicated by arrows.

As discussed above, different strategies have been devised to improve the specificity of CRISPR-Cas9 genome modification.

FIG. 2A shows a paired nickase strategy using two copies of a Cas9 mutant (Cas9-D10A) 240, 242 in a CRISPR:Cas9-D10A system 202A. The system 202A makes offset single-stranded nicks at two DNA target sites directed by two distinct guide RNA sequences. A first single-guide RNA 204 has a 20-nt guide sequence at the 5' end 206, which is complementary to a 20-bp target sequence 218 in DNA, a 3' domain 208 that binds the first Cas9-D10A 240, and a hairpin or duplex structure 210 between the 5' and 3' domains. The Cas9-D10A:guide RNA complex binds a target DNA 216 containing a protospacer 222 directly upstream of a 3-nt PAM site 224. A first target DNA sequence 218 in the target DNA 216 is cleaved by Cas9-D10A 240 at the site 226 indicated by arrows but its complementary strand is not cleaved. The system 202A also comprises a second single-guide RNA 228 has a 20-nt guide sequence at the 5' end 230, which is complementary to a second 20-bp target sequence 238 in DNA, a 3' domain 232 that binds the second Cas9-D10A 242, and a hairpin or duplex structure 234 between the 5' and 3' domains. The Cas9-D10A:guide RNA complex binds and cleaves a target DNA 236 containing a protospacer 244 directly upstream of a 3-nt PAM site 246. A second target DNA sequence 238 on a strand opposite the strand having the first target DNA sequence 218 is cleaved by Cas9-D10A 242 at the site 248 indicated by arrows but its complementary strand is not cleaved. By action of the two Cas9-D10A nickases 240, 242, a double stranded break is made in a double stranded DNA.

FIG. 2B shows the dimeric RNA-guided FokI nuclease strategy in which catalytically inactive Cas9 proteins (dCas9) 250, 252 are fused to dimerization-dependent FokI nuclease domains 256, 260. The CRISPR:dCas9-FokI system 202B comprises a first single-guide RNA 204 having a 20-nt guide sequence at the 5' end 206, which is complementary to a first target sequence 218 in a first target DNA 216, a 3' domain 208 that binds the first dCas9 250, and a hairpin or duplex structure 210 between the 5' and 3' domains. The first dCas9:guide RNA complex binds a target DNA 216 containing a protospacer 222 directly upstream of a 3-nt PAM site 224. The system 202B also comprises a second single-guide RNA 228 having a 20-nt guide sequence at the 5' end 230, which is complementary to a second target sequence 238, a 3' domain 232 that binds the second dCas9 252, and a hairpin or duplex structure 234 between the 5' and 3' domains. The second dCas9:guide RNA complex binds a target DNA 236 containing a protospacer 242 directly upstream of a 3-nt PAM site 244. A first peptide linker 254 links a first FokI domain 256 to the first dCas9 250, and a second peptide linker 258 links a second FokI domain 260 to the second dCas9 252. The two guide RNAs 204, 228 direct the dCas9-FokI fusion proteins to dimerize and cleave both strands of target DNA 216, 236 at the cleavage site 226.

FIG. 2C shows a truncated guide RNA approach which removes 2 or 3 nt from the 5' end of the guide RNA but does not modify the Cas9 protein 220. The CRISPR-Cas9 system 202C has a single-guide RNA 205 has a 17-nt or 18-nt guide sequence at the 5' end 206, which is complementary to a 20-bp target sequence 218 in DNA. Use of truncated gRNAs can reduce off-target effects. The truncated single-guide RNA 205 also has a 3' domain 208 that binds the first Cas9-D10A 240, and a hairpin or duplex structure 210 between the 5' and 3' domains. The Cas9:guide RNA complex binds a target DNA 216 containing a protospacer 222 directly upstream of a 3-nt PAM site 224. The target DNA sequence 218 in the target DNA 216 and its complementary strand are cleaved by Cas9 240 to form a double-stranded break at the site 226 indicated by arrows.

III. Engineered Guide RNA

Due to its simplicity and efficiency over others, the CRISPR-Cas system has been used to perform genome-editing in cells of various organisms. Yet, as the specificity of this system is dictated by base-pairing between a target DNA and a custom-designed guide RNA, and the system tolerates base-pair mismatching between the target DNA and the guide RNA, undesired off-target DNA binding and cleavage limit the application of this system. By engineering and adjusting the base-pairing properties of guide RNAs, this invention aims to reduce off-target binding and/or cleavage while maintaining or even enhancing on-target activity of CRISPR-Cas systems.

The engineered guide RNA of this invention has at least a guide sequence, a blocking sequence, and optionally a linker joining the guide sequence and the blocking sequence. In the absence of a target sequence, the blocking sequence hybridizes to at least a portion of the guide sequence. However, when target sites and off-target sites are present, the blocking sequence competes with them for the guide sequence, and the thermodynamically favored sequences will more likely bind the guide sequence, out-competing off-target sites. The components of the guide RNA are discussed below.

1. Guide Sequence

Among the components of the guide RNA disclosed herein, the guide sequence provides the targeting specificity. It includes a region that is complementary and capable of hybridization to a pre-selected target site of interest. In various embodiments, this guide sequence can comprise from about 10 nucleotides to more than about 25 nucleotides. For example, the region of base pairing between the guide sequence and the corresponding target site sequence can be about 10, 11, 12, 13, 14, 15, 16, 17, 18, 19, 20, 22, 23, 24, 25, or more than 25 nucleotides in length. In an exemplary embodiment, the guide sequence is about 17-20 nucleotides in length, such as 20 nucleotides.

One requirement for selecting a suitable target nucleic acid is that it has a 3' PAM site/sequence. Each target sequence and its corresponding PAM site/sequence are referred herein as a Cas-targeted site. Type II CRISPR system, one of the most well characterized systems, needs only Cas 9 protein and a guide RNA complementary to a target sequence to affect target cleavage. The type II CRISPR system of *S. pyogenes* uses target sites having N12-20NGG, where NGG represent the PAM site from *S. pyogenes*, and N12-20 represents the 12-20 nucleotides directly 5' to the PAM site. Additional PAM site sequences from other species of bacteria include NGGNG, NNNNGATT, NNAGAA, NNAGAAW, and NAAAAC, where N is any nucleotide (standard or modified) and W is a nucleotide with weak interactions, such as A or T/U. See, e.g., US 20140273233, WO 2013176772, Cong et al., (2012), Science 339 (6121): 819-823, Jinek et al., (2012), Science 337 (6096): 816-821, Mali et al, (2013), Science 339 (6121): 823-826, Gasiunas et al., (2012), Proc Natl Acad Sci USA. 109 (39): E2579-E2586, Cho et al., (2013) Nature Biotechnology 31, 230-232, Hou et al., Proc Natl Acad Sci USA. 2013 Sep. 24; 110(39):15644-9, Mojica et al., Microbiology. 2009 March; 155(Pt 3):733-40, and www.addgene.org/CRISPR/.

The target nucleic acid strand can be either of the two stands on a genomic DNA in a host cell. Examples of such genomic dsDNA include, but are not necessarily limited to, a host cell chromosome, mitochondrial DNA and a stably maintained plasmid. However, it is to be understood that the present method can be practiced on other dsDNA present in a host cell, such as non-stable plasmid DNA, viral DNA, and phagemid DNA, as long as there is Cas-targeted site regardless of the nature of the host cell dsDNA.

2. Blocking Sequence

The second component of the guide RNA disclosed herein is a cis-blocking sequence, which is complementary and capable of hybridization to at least a portion of the above-described guide sequence. The blocking sequence can be 5-20 nucleotides long, e.g., 5, 6, 7, 8, 9, 10, 11, 12, 13, 14, 15, 16, 17, 18, 19, or 20 nucleotides in length. In the absence of the target of the guide sequence, the cis-blocking sequence hybridizes to the guide sequence and forms a duplex stem. The formation of the stem makes fewer nucleotides on the guide sequence available to both target and non-target sequences, but unzipping of the stem is more thermodynamically favorable for hybridization of the target sequence to the guide sequence, and hybridization of the guide sequence to non-target sequences is thus reduced.

To that end, computational analysis of the thermodynamic secondary structural properties of the guide sequence and/or the entire guide RNA as a whole can be used to create a cis-blocking sequence (FIG. 3). For example, GC content and/or length of the blocking sequence can be used to achieve the desired level of binding affinity. Utilizing standard and/or modified nucleotides, the cis-blocking sequence can be designed to weakly base pair with part of the guide sequence of the guide RNA, thereby sequestering this region from binding to off-target DNA sequences that only partially match the guide sequence. Such weak base-pairing in the cis-blocked stem will be out-competed and melted by a fully cognate DNA target sequence when the cis-blocked guide RNA-Cas9 complex recognizes the on-target sequence. Thus, Cas9-guided binding and/or cleavage of a cognate DNA target occurs with improved specificity when a well-designed cis-blocking sequence is included. The blocking sequence may be 3' or 5' with respect to the guide sequence if they are in the same RNA molecule. If the guide RNA consists of two or more RNA molecules, they can be in separate RNA molecules.

3. Linker

In certain embodiments of the guide RNA of this invention, the above-described guide sequence and the cis-blocking sequence are joined by a linker sequence. Such as linker can be a polynucleotide linker or non-nucleotide linker or a combination thereof.

In one embodiment, the linker is a nucleotide linker, and can be at least 1 nucleotide in length, such as 4-20 nucleotides in length, e.g., 4 (tetraloop), 5, 6, 7, 8, 9, 10, 11, 12, 13, 14, 15, 16, 17, 18, 19, or 20. Any nucleotides can be used to make the linker as long as they do not interfere with duplex formation between the guide sequence and the blocking sequence or otherwise interfere with the activity of a guide RNA-Cas9 complex.

In another embodiment, the linker is a non-nucleotide linker, which can comprise abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., WO 89/02439; Usman et al., WO 95/06731; Dudycz et al., WO 95/11910 and Ferentz and Verdine, J. Am. Chem. Soc. 1991, 113:4000. A "non-nucleotide" further means any chemical group or compound that can be incorporated into a nucleic acid chain in the place of one or more nucleotide units, including either sugar and/or phosphate substitutions, and allows the remaining bases to exhibit their target recognition activity. The group or compound can be abasic in that it does not contain a commonly recognized nucleotide base, such as adenosine, guanine, cytosine, uracil or thymine, for example at the C1 position of the sugar. In some embodiments, the linker includes one or more spacers selected from the group consisting of a hexanediol spacer, a TEG spacer, a C3 spacer, and a poly A spacer.

4. Additional Components

Besides the above-described guide sequence, blocking sequence, and linker, the guide RNA of this invention can include additional active or non-active components. In one example, the guide RNA has a tracrRNA activity. For example, the guide RNA can be a hybrid RNA molecule where the above-described components are fused to a tracrRNA to mimic the natural crRNA:tracrRNA duplex. Shown below is an exemplary hybrid crRNA:tracrRNA, sgRNA sequence: 5'-(20nt guide)-GUUUAAGAGCUAUGCUG-GAAACAG CAUAGCAAGUUUAAAUAAGGCUAGU-CCGUUAUCAACUUGAAAAGUGGCACCGAG UCG-GUGCUUUUUUU-3' (SEQ ID NO:2) (Chen et al. Cell. 2013 Dec. 19; 155(7):1479-91. doi: 10.1016/j.cell.2013.12.001.), which can be linked, optionally with a linker, to a blocking sequence described above. Various tracrRNA sequences are known in the art and examples include the following tracrRNAs and active portions thereof. As used herein, an active portion of a tracrRNA retains the ability to form a complex with a Cas protein, such as Cas9 or dCas9. See, e.g., WO2014144592. Methods for generating crRNA-tracrRNA hybrid RNAs are known in the art. See e.g., WO2014099750, US 20140179006, and US 20140273226.

```
                                            (SEQ ID NO: 3)
GGAACCAUUCAAAACAGCAUAGCAAGUUAAAAUAAGGCUAGUCCGU
UAUCAACUUGAAAAGUGGCACCGAGUCGGUGC;

(SEQ ID NO: 4)
UAGCAAGUUAAAAUAAGGCUAGUCCGUUAUCAACUUGAAAAAGUGG
CACCGAGUCGGUGC;

(SEQ ID NO: 5)
AGCAUAGCAAGUUAAAAUAAGGCUAGUCCGUUAUCAACUUGAAAAA
GUGGCACCGAGUCGGUGC;;

(SEQ ID NO: 6)
CAAAACAGCAUAGCAAGUUAAAAUAAGGCUAGUCCGUUAUCAACUU
GAAAAAGUGGCACCGAGUCGGUGC;

(SEQ ID NO: 7)
UAGCAAGUUAAAAUAAGGCUAGUCCGUUAUCAACUUGAAAAAGUG;

(SEQ ID NO: 8)
UAGCAAGUUAAAAUAAGGCUAGUCCGUUAUCA;
and (SEQ ID NO: 9)
UAGCAAGUUAAAAUAAGGCUAGUCCG.
```

In some embodiments, the tracrRNA activity and the guide sequence are included in two separate RNA molecules, which together form the guide RNA. In this case, the molecule with the tracrRNA activity should be able to interact with (usually by base pairing) the molecule having the guide sequence.

The guide RNA of this invention can be made by various methods known in the art including cell-based expression, in vitro transcription, and chemical synthesis. The ability to chemically synthesize relatively long RNAs (as long as 200 mers or more) using TC-RNA chemistry (see, e.g., U.S. Pat. No. 8,202,983) allows one to produce guide RNAs with special features that outperform those enabled by the basic four ribonucleotides (A, C, G and U). For example, the single-stranded linker between the 20-nt guide sequence and the cis-blocking sequence can be synthesized of molecules that cannot base pair, precluding the linker from deleterious misfolding and/or off-target sequence recognition.

Another advantage of chemically synthesizing the cis-blocking sequence is that synthesis allows adjustment of the base-pairing strength of the blocking sequence, specifically by installing one or more modified nucleotides in the blocking sequence to adjust its base-pairing potential. For example, RNA-RNA stems are more stable and have a higher Tm than RNA-DNA stems of the same sequence. Accordingly, chemical synthesis of the blocking sequence allows one to install one or more deoxyribonucleotides at select sites in the sequence to weaken its base pairing with the 20-nt guide sequence. In addition to the option of including 2'-deoxynucleotides, one can incorporate other chemical modifications known to raise or lower the Tm of base pairing. Chemical modifications known to stabilize base pairing include the following: 2'-O-methyl, 2'-fluoro, 2-thiouridine, 4-thiouridine, 2-aminoadenine, and LNA (locked nucleic acid) substituents. Chemical modifications known to weaken base pairing include phosphorothioate, phosphorodithioate, phosphonoacetate (PACE), boranophosphonate, methylphosphonate, and UNA (unlocked nucleic acid) substituents.

Modified RNA oligonucleotides such as locked nucleic acids (LNAs) have been demonstrated to increase the specificity of RNA-DNA hybridization by locking the modified oligonucleotides in a more favorable (stable) conformation. For example, LNA-modified RNA has a modified ribose sugar comprising an additional covalent linkage between the 2' oxygen and 4' carbon which when incorporated into oligonucleotides can improve overall thermal stability and selectivity. Thus in some embodiments, the guide RNAs disclosed herein may comprise one or more modified RNA oligonucleotides. For example, the guide RNA can have chemical modifications in one, some or all of the nucleotides in the guide region or blocking region. Examples of chemically modified nucleotides for RNA include a locked (2'-O-4'-C methylene bridge) nucleotide, 5-methylcytidine, 2'-O-methyl nucleotide, pseudouridine, or a nucleotide in which the ribose phosphate backbone has been replaced by a polyamide chain (peptide nucleic acid), e.g., a synthetic ribonucleic acid.

Existing CRISPR-Cas systems use guide RNA-DNA heteroduplex formation to guide targeting to genomic sites of interest. However, RNA-DNA heteroduplexes can form a more promiscuous range of structures than their DNA-DNA counterparts. In contrast, DNA-DNA duplexes are more sensitive to mismatches, and therefore a DNA-guided nuclease may not bind as readily to off-target sequences, making them comparatively more specific than RNA-guided nucleases. Thus, the guide RNAs described herein can be hybrids, i.e., wherein one or more deoxyribonucleotides, e.g., a short DNA oligonucleotide, replaces all or part of the guide RNA, e.g., all or part of the guide sequence of a guide RNA. In a system where the guide RNA comprises two RNA molecules, one or both can be synthetic and include one or more modified (e.g., locked) nucleotides or deoxyribonucleotides. A system that incorporates DNA into the guide sequence should more reliably target the intended genomic DNA sequences due to the general intolerance of DNA-DNA mismatching, compared to RNA-DNA duplexes. Methods for making such chimeras are known in the art, See, e.g., Barker et al, BMC Genomics. 2005 Apr. 22; 6:57; and Sugimoto et al, Biochemistry. 2000 Sep. 19; 39(37): 11270-81.

By site-specific incorporation of base pair-strengthening and/or -weakening modifications in the blocking sequence or guide sequence, the thermodynamic stability of a cis-blocked stem can be finely tuned to enhance guide RNA specificity without substantially reducing its on-target activity. Other parts of the guide RNA can be modified as well.

Shown in FIGS. 3A to 3D are exemplary CRISPR-Cas systems 302A to 302D with engineered guide RNAs of this invention. More specifically, for each DNA target sequence, a specific blocking sequence 314 is tethered via a linker 312 to the 5' end of the guide RNA 304 and is designed to hybridize to a portion of the 20-nt guide sequence of the guide RNA 304. In the absence of the target sequence, the blocking sequence 314 hybridizes with a portion of the DNA-binding region of the guide RNA 304 to form a stem 366 and sequesters that portion. In the presence of target sequences 318, this cis-blocked stem 366 thwarts base pairing of the guide RNA with off-target DNA sequences 364 (black segments shown in FIGS. 3A-3C) that may share a high level of homology with an intended target site 318.

The systems include a tracrRNA 308 which may be part of a single-guide RNA 304 having a hairpin or duplex structure 310 between the 5' and 3' domains. The guide RNA 304 binds a Cas9 nuclease 320 to form a complex. The Cas9: guide RNA complex binds a target DNA 316 having a protospacer 322 and a PAM 324, as well as off-target DNA 362 having homology to the target DNA (shown in FIG. 3A-3C).

The blocking sequence 314 can be rationally designed to form base pairs with various portions of the 20-nt DNA-binding region (1 to 20 in FIGS. 3A to 3C). The flexibility of the design allows one to customize blocking sequences 314 to bind and sequester different regions of a 20-nt guide sequence, such as the 5' region (FIG. 3A) or 3' region (FIG. 3B) or a middle region, to adjust the specificity of guide RNA binding and/or cleavage.

The length and/or composition of the blocking sequence 314 can also be varied, as well as the linker element 312 (FIGS. 3A-3D, gray line) connecting the blocking and guide sequences. To that end, one can further customize the length and composition of the blocking sequence, the guide RNA sequence, and/or the intervening linker element, to modulate the thermodynamic strength of the hybridization between the blocking sequence and the DNA-targeting sequence of the guide RNA 304.

In the presence of a cognate DNA target, the cis-blocked stem 316 unwinds as the DNA target hybridizes with the guide sequence, leading to Cas9 cleavage. As shown in FIG. 3D, a cognate DNA target site 318 (which is fully complementary to the 20-nt guide sequence) can hybridize to all 20 nt 306 of the guide sequence 304 while the cis-blocked guide RNA duplex is disfavored, thereby allowing binding of Cas9 320 and cleavage 326 of the targeted site.

Conversely, the cis-blocked guide RNA duplex is designed such that off-target sites 362 with partial complementarity to the guide sequence are less likely to disrupt the cis-blocked duplex, thus impeding Cas9 binding and/or cleavage of off-target sites. For example, see FIGS. 3A-3C. Shown in FIG. 3A are an off-target site 362 of 20 bp and a cis-blocked guide RNA 304 of this invention. The off-target site and guide RNA have mismatches 364 (black segment). In the guide RNA, 5 nt of the guide sequence base-pairs with the blocking sequence and forms a 5-bp duplex, while the rest 15 nt of the guide sequence 366 hybridize to the off-target site and form 15 bp duplex. Guide RNA:DNA target hybridization of 15 bp or less (such as the partially hybridizing sequence 366) is known to abolish Cas9 nuclease activity (Fu et al., (2014) *Nat. Biotechnol.*, 32, 279-84). Accordingly, the engineered guide RNAs of this invention and related CRISPR-Cas systems 302A to 302D allow one to reduce off-target base-pairing and increase the specificity.

In addition to reducing off-target base-pairing and increasing specificity, the engineered guide RNA of this invention and related CRISPR-Cas system also allow one to increase the on-target activity of the CRISPR-Cas complex. It was found that addition of random bases upstream of the 5' end of guide RNAs increased Cas9-mediated homologous recombination (HR), likely due to an increase in Cas9-induced double-stranded cleavage near the site of HR (Mali et al., (2013) *Nat. Biotechnol.*, 31, 833-8). Also, the hairpin structure of the cis-blocked duplex can protect the guide RNA against 5' exonucleolytic degradation, allowing more of the guide RNA introduced to yield on-target effects. Furthermore, as disclosed herein, cis-blocked DNA-guide RNA chimeras will be more stable in vivo, as DNA molecules are less susceptible to cellular degradation processes.

Unlike previous strategies to increase Cas9:guide RNA cleavage specificity, the cis-blocked guide RNA approach of this invention minimizes any reduction in on-target cleavage activity, yielding better results than most Cas9:guide RNA designs described to date. As mentioned above, appending a blocking sequence to the 5' end of the guide RNA can increase the in vivo stability of the guide RNA by thwarting 5' exonucleases present in cells and sometimes in in vitro preps if contaminated. Although a systematic study of guide RNA structures and their resulting CRISPR-Cas activities has not been published, it is presumed that misfolding of the guide RNA could decrease Cas9 loading and therefore CRISPR-Cas efficacy. The invention disclosed herein protects part of the variable 20-nt guide sequence in a cis-blocking hairpin (FIG. 3A), which should promote correct folding of the remainder sequence of guide RNAs, known to bind Cas9 protein (FIG. 1). Finally, in contrast to known strategies that employ paired Cas9 nickases or dimeric dCas9-FokI nucleases, both of which require two guide RNA sequences targeted to appropriately spaced PAM sites, a cis-blocked guide RNA will function with just one PAM-addressable site, making it applicable to a greater number of loci.

The cis-blocked guide RNA approach of this invention can be incorporated into previous strategies intended to increase Cas9:guide RNA cleavage specificity. For example, a blocking sequence can be linked, optionally through a linker, to the first guide RNA 204 and/or the second guide RNA 228 of the CRISPR:Cas9-D10A system 202A, to the first guide RNA 204 and/or the second guide RNA 228 of CRISPR:dCas9-FokI system 202B, or to the truncated guide RNA 205 of the CRISPR:Cas9 system 202C.

IV. RNA-CRISPR/Cas Protein Complex and Related Systems

1. CRISPR/Cas Protein Complex

The invention in one embodiment further provides a guide RNA-CRISPR/Cas protein complex. This complex in general includes three components: (i) a component for enzymatic cleaving or nicking, or binding of a target double-stranded nucleic acid at a specific sequence, (ii) a targeting component comprising a guide sequence, which directs the complex to the correct target sequence, and (iii) a tracr component that recognizes and binds the first component. The first component can be a CRISPR/Cas protein while the latter two can be provided by the above-discussed guide RNA. These two RNAs can be provided as one hybrid RNA molecule known in the art as a single guide RNA (or "sgRNA"), or as two separate RNA molecules.

A CRISPR protein or Cas protein, used interchangeably, refers to a protein of or derived from a CRISPR-Cas type I, type II, or type III system, which has an RNA-guided DNA-binding and/or nuclease activity. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. See e.g., WO2014144761 WO2014144592, WO2013176772, US20140273226, and US20140273233, the contents of which are incorporated herein by reference in their entireties.

In one embodiment, the CRISPR protein is derived from a type II CRISPR-Cas system. In exemplary embodiments, the CRISPR or Cas protein is or is derived from a Cas9 protein. The Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Staphylococcus aureus, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigenci, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina*.

In general, a CRISPR/Cas protein includes at least one RNA binding domain. RNA binding domains interact with the guide RNA. The CRISPR protein can be a wild type CRISPR protein or a modified CRISPR protein. The CRISPR protein can be modified to increase nucleic acid binding affinity and/or specificity, alter an enzymatic activity, and/or change another property of the protein. For example, nuclease (i.e., DNase, RNase) domains of the CRISPR protein can be modified, deleted, or inactivated. Alternatively, the CRISPR protein can be truncated to remove domains that are not essential for the function of the protein. The CRISPR protein can also be truncated or modified to optimize the activity of the effector domain.

In some embodiments, the CRISPR protein can be a mutant of a wild type CRISPR protein (such as Cas9) or a fragment thereof. Examples of known mutants of Cas9 include the Cas9 nickases such as Cas9-D10A, cleavage-deactivated dCas9, Cas9 mutants with altered PAM specificity such as those disclosed in Kleinstiver et al., "Engineered CRISPR-Cas9 nucleases with altered PAM specificities", Nature 523, 481-485 (2015) (e.g., D1135E SpCas9), Cas9 mutants from *Staphylococcus aureus* (SaCas9) such as those disclosed in Ran et al., "In vivo genome editing using *Staphylococcus aureus* Cas9", Nature 520, 186-191 (2015). In other embodiments, the CRISPR protein can be derived from a mutant CRISPR protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein. In some embodiments, the present system utilizes the Cas9 protein from *S. pyogenes*, either as encoded in bacteria or codon-optimized for expression in mammalian cells. Shown below is the amino acid sequence of wild type *S pyogenes* Cas9 protein sequence (SEQ ID NO: 1, available at www.uniprot.org/uniprot/Q99ZW2), sometimes referred to as (SpCas9).

```
                                            (SEQ ID NO: 1)
MDKKYSIGLDIGTNSVGWAVITDEYKVPSKKFKVLGNTDRHSIKKN

LIGALLFDSGETAEATRLKRTARRRYTRRKNRICYLQEIFSNEMAK

VDDSFFHRLEESFLVEEDKKHERHPIFGNIVDEVAYHEKYPTIYHL

RKKLVDSTDKADLRLIYLALAHMIKFRGHFLIEGDLNPDNSDVDKL

FIQLVQTYNQLFEENPINASGVDAKAILSARLSKSRRLENLIAQLP

GEKKNGLFGNLIALSLGLTPNEKSNFDLAEDAKLQLSKDTYDDDLD

NLLAQIGDQYADLFLAAKNLSDAILLSDILRVNTEITKAPLSASMI

KRYDEHHQDLTLLKALVRQQLPEKYKEIFFDQSKNGYAGYIDGGAS

QEEFYKFIKPILEKMDGTEELLVKLNREDLLRKQRTFDNGSIPHQI

HLGELHAILRRQEDFYPFLKDNREKIEKILTFRIPYYVGPLARGNS

RFAWMTRKSEETITPWNFEEVVDKGASAQSFIERMTNFDKNLPNEK

VLPKHSLLYEYFTVYNELTKVKYVTEGMRKPAFLSGEQKKAIVDLL

FKTNRKVTVKQLKEDYFKKIECFDSVEISGVEDRFNASLGTYHDLL

KIIKDKDFLDNEENEDILEDIVLTLTLFEDREMIEERLKTYAHLFD

DKVMKQLKRRRYTGWGRLSRKLINGIRDKQSGKTILDFLKSDGFAN

RNFMQLIHDDSLTFKEDIQKAQVSGQGDSLHEHIANLAGSPAIKKG

ILQTVKVVDELVKVMGRHKPENIVIEMARENQTTQKGQKNSRERMK

RIEEGIKELGSQILKEHPVENTQLQNEKLYLYYLQNGRDMYVDQEL

DINRLSDYDVDHIVPQSFLKDDSIDNKVLTRSDKNRGKSDNVPSEE

VVKKMKNYWRQLLNAKLITQRKFDNLTKAERGGLSELDKAGFIKRQ

LVETRQITKHVAQILDSRMNTKYDENDKLIREVKVITLKSKLVSDF

RKDFQFYKVREINNYHHAHDAYLNAVVGTALIKKYPKLESEFVYGD

YKVYDVRKMIAKSEQEIGKATAKYFFYSNIMNFFKTEITLANGEIR

KRPLIETNGETGEIVWDKGRDFATVRKVLSMPQVNIVKKTEVQTGG

FSKESILPKRNSDKLIARKKDWDPKKYGGFDSPTVAYSVLVVAKVE

KGKSKKLKSVKELLGITIMERSSFEKNPIDFLEAKGYKEVKKDLII

KLPKYSLFELENGRKRMLASAGELQKGNELALPSKYVNFLYLASHY

EKLKGSPEDNEQKQLFVEQHKHYLDEIIEQISEFSKRVILADANLD

KVLSAYNKHRDKPIREQAENIIHLFTLTNLGAPAAFKYFDTTIDRK

RYTSTKEVLDATLIHQSITGLYETRIDLSQLGGD
```

A mutant of a wild type Cas protein refers to a polypeptide derivative of the wild type protein, e.g., a protein having one or more point mutations, insertions, deletions, truncations, a fusion protein, or a combination thereof. The mutant has at least one of the RNA-guided DNA binding activity, or RNA-guided nuclease activity, or both. In general, the modified version is at least 50% (e.g., any number between 50% and 100%, inclusive, e.g., 50%, 60%, 70%, 75%, 80%, 85%, 90%, 95%, and 99%) identical to the wild type protein such as SEQ ID NO:1.

A CRISPR/Cas protein described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6×-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the polypeptides/proteins can be chemically synthesized (see e.g., Creighton, "Proteins; Structures and Molecular Principles," W.H. Freeman & Co., NY, 1983), or produced by recombinant DNA technology as described herein. For additional guidance, skilled artisans may consult Frederick M. Ausubel et al., Current Protocols in Molecular Biology, John Wiley & Sons, 2003; and Sambrook et al., Molecular Cloning, A Laboratory Manual," Cold Spring Harbor Press, Cold Spring Harbor, N.Y., 2001).

The CRISPR/Cas protein described in the invention can be provided in purified or isolated form, or can be part of a composition. Preferably, where in a composition, the proteins are first purified to some extent, more preferably to a high level of purity (e.g., about 80%, 90%, 95%, or 99% or higher). Compositions according to the invention can be any type of composition desired, but typically are aqueous compositions suitable for use as, or inclusion in, a composition for RNA-guided nuclease reaction. Those of skill in the art are well aware of the various substances that can be included in such nuclease reaction compositions.

CRISPR/Cas protein-guide RNA complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties. The complexes can be isolated or purified, at least to some extent, from cellular material of a cell or an in vitro translation-transcription system in which they are produced.

2. Nucleic Acids, Vectors, and Host Cells

To use the guide RNAs and complexes described above, it may be desirable to express them from a nucleic acid that encodes them. This can be performed in a variety of ways. For example, the nucleic acid encoding the guide RNA can be cloned into an intermediate vector for transformation into prokaryotic or eukaryotic cells for replication and/or transcription. Intermediate vectors are typically prokaryotic vectors, e.g., plasmids, or shuttle vectors, or insect vectors, for storage or manipulation of the nucleic acid encoding the guide RNA for production of the guide RNA. The nucleic acid encoding the guide RNA can also be cloned into an expression vector, for administration to a plant cell, animal cell, preferably a mammalian cell or a human cell, fungal cell, bacterial cell, or protozoan cell. Accordingly, the present invention provides a nucleic acid that encodes any of the guide RNAs mentioned above. Preferably, the nucleic acid is isolated and/or purified.

The present invention also provides recombinant constructs or vectors having sequences encoding one or more of the guide RNAs or proteins described above. Examples of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in e.g., Sambrook et al. (2001, Molecular Cloning: A Laboratory Manual, Cold Spring Harbor Press).

A vector refers to a nucleic acid molecule capable of transporting another nucleic acid to which it has been linked. The vector can be capable of autonomous replication or integration into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as inducible regulatory sequences. The design of the expression vector can depend on such factors as the choice of the host cell to be transformed, transfected, or infected, the level of expression of guide RNAs or protein desired, and the like.

Examples of expression vectors include chromosomal, nonchromosomal and synthetic DNA sequences, bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the RNAs or polypeptides described above can be inserted into an appropriate restriction endonuclease site(s) by procedures known in the art. Such procedures and related sub-cloning procedures are within the scope of those skilled in the art.

The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

The vectors for expressing the guide RNAs can include RNA Pol III promoters to drive expression of the guide RNAs, e.g., the HI, U6 or 7SK promoters. These human promoters allow for expression of guide RNAs in mammalian cells following plasmid transfection. Alternatively, a T7 promoter may be used, e.g., for in vitro transcription, and the RNA can be transcribed in vitro and purified. Vectors suitable for the expression of short RNAs, e.g., siRNAs, shRNAs, or other small RNAs, can be used.

The vector containing the appropriate nucleic acid sequences as described above, as well as an appropriate promoter or control sequence, can be employed to transform, transfect, or infect an appropriate host to permit the host to express the RNAs or polypeptides described above. Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned RNAs or polypeptides by transforming, transfecting, or infecting a host cell with an expression vector having a nucleotide sequence that encodes one of the RNAs or polypeptides. The host cells are then cultured under a suitable condition, which allows for the expression of the RNAs or polypeptides.

Any of the procedures known in the art for introducing foreign nucleotide sequences into host cells may be used. Examples include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell.

3. Libraries

The present invention also provides a library of multiple guide RNAs. The library contains two or more of the engineered guide RNAs or RNA sets disclosed herein. Also provided is a library containing multiple nucleic acids encoding the RNAs or RNA sets. For example, such a library can contain a library of recombinant expression vectors comprising nucleotides encoding the RNAs or RNA sets. The library can contain from about 10 to about $10^{12}$ individual members, e.g., 10 to about $10^2$, about $10^2$ to about $10^3$, about $10^3$ to about $10^5$, from about $10^5$ to about $10^7$, from about $10^7$ to about $10^9$, or from about $10^9$ to about $10^{12}$ members. An individual member of the library differs from other members of the library in the guide sequence, i.e., the DNA targeting segment of the RNA, or in the blocking sequence. On the other hand, each individual member of a library can contain the same or substantially the same nucleotide sequence of the CRISPR/Cas protein-binding segment as all other members of the library. In this way, the library can comprise members that bind to different target nucleic acids.

As the engineered guide RNAs or RNA sets disclosed herein reduce off-target base-pairings and increase the specificity and on-target activity of the CRISPR-Cas complex, the library allows one to conduct high through-put genomic manipulation and analysis, in which only the DNA-targeting segments of the guide RNAs need to be varied, while the protein-binding segment can be the same. Accordingly, one can carry out a large-scale gene-editing by specifically manipulating or modifying multiple targets at the same time.

4. Kits

This invention further provides kits containing reagents for performing the above-described methods, including CRISPR:Cas guided target binding or nuclease reaction. To that end, one or more of the reaction components, e.g., guide RNAs and Cas proteins, for the methods disclosed herein can be supplied in the form of a kit for use. In one embodiment, the kit comprises a CRISPR protein or a nucleic acid encoding the CRISPR protein, and one or more of a guide RNA described above, a set of RNA molecules described above, and a library described above. In others embodiments, the kit can include one or more other reaction components. In such a kit, an appropriate amount of one or more reaction components is provided in one or more containers or held on a substrate.

Examples of additional components of the kits include, but are not limited to, one or more different polymerases, one or more host cells, one or more reagents for introducing foreign nucleotide sequences into host cells, one or more reagents (e.g., probes or PCR primers) for detecting expression of the RNA or Cas protein or verifying the target nucleic acid's status, and buffers or culture media for the reactions (in 1× or concentrated forms). The kit may also include one or more of the following components: supports, terminating, modifying or digestion reagents, osmolytes, and an apparatus for detection.

The reaction components used can be provided in a variety of forms. For example, the components (e.g., enzymes, RNAs, probes and/or primers) can be suspended in an aqueous solution or as a freeze-dried or lyophilized powder, pellet, or bead. In the latter case, the components, when reconstituted, form a complete mixture of components for use in an assay. The kits of the invention can be provided at any suitable temperature. For example, for storage of kits containing protein components or complexes thereof in a liquid, it is preferred that they are provided and maintained below 0° C., preferably at or below −20° C., or otherwise in a frozen state.

A kit or system may contain, in an amount sufficient for at least one assay, any combination of the components described herein. In some applications, one or more reaction components may be provided in pre-measured single use amounts in individual, typically disposable, tubes or equivalent containers. With such an arrangement, a RNA-guided nuclease reaction can be performed by adding a target nucleic acid, or a sample or cell containing the target nucleic acid, to the individual tubes directly. The amount of a component supplied in the kit can be any appropriate amount and may depend on the target market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

V. Uses

As described above, CRISPR/Cas RNA-guided nucleases based on conventional guide RNA can have significant off-target mutagenic effects. Such off-target effects can be problematic for research and in particular for potential therapeutic applications. Therefore, methods for improving the specificity of CRISPR-Cas RNA guided nuclease system are needed.

The present application provides a method for improving the specificity of CRISPR-Cas guided nuclease system based on a seemingly counterintuitive idea of including a blocking sequence in a guide RNA, which is complementary to a portion of the guide RNA, thereby shortening, rather than lengthening, the guide RNA complementarity region available to base-pair with the corresponding target sequence. The idea may be counterintuitive and unexpected since it was well understood that for short hybridizing sequences, a longer complementarity region would lead to higher hybridization specificity. Yet, as disclosed herein, by shortening the complementarity region available to base-pair with the target, the approach of this invention decreases the stability of the guide RNA:target DNA hybrid, making it less tolerant of mismatches and thereby making the targeting more specific. That is, adding additional sequence to the guide RNA sequence actually results in a RNA-guided nuclease that is less tolerant to even single nucleotide mismatches and therefore more specific and has fewer unintended off-target effects.

The approach of this invention is counterintuitive also in that it was previously reported that lengthening the 5' end of the guide RNA makes it function less efficiently at the on-target site (Ran et al, *Cell*. 2013 Sep. 12; 154(6): 1380-9). However, as disclosed herein, the guide RNA and related methods enhance efficiency of CRISPR/Cas RNA-guided nucleases reaction and on-target genome editing by adding blocking sequences to guide RNAs.

These blocked guide RNAs can induce various types of Cas-mediated on-target genome editing events with efficiencies comparable to (or, in some cases, higher than) non-blocked guide RNAs at cognate target sites in vitro or in vivo (e.g., in reporter gene or in endogenous cellular genes). Most importantly, use of blocked guide RNAs substantially reduces off-target effects, yielding improvements of specificity. Thus, the blocked guide RNAs and related methods of this invention provide a highly effective approach for reducing off-target effects without compromising on-target activity and without the need for a second, potentially mutagenic guide RNA. This approach can be implemented on its own or in conjunction with other strategies such as paired nickase method as shown in FIG. 2A to reduce the off-target effects of CRISPR-Cas system.

This method of the invention can be used with CRISPR protein other than *S. pyogenes* Cas9, including other Cas proteins from bacteria or archaea as well as Cas9 variants that nick a single strand of DNA or have no nuclease activity, such as the above-mentioned cleavage-deactivated Cas9 bearing catalysis-inactivating mutations in one or both nuclease domains. This method can be applied to systems that utilize a single guide RNA as well as those that use dual RNAs (e.g., the crRNA and tracrRNA activities found in naturally occurring systems).

In one aspect, the method and guide RNA described above can be used for modifying a chromosomal sequence in a cell, embryo, or animal. The method comprises contacting or introducing into the cell or embryo (a) one or more RNA-guided endonucleases or nucleic acid encoding the RNA-guided endonucleases and (b) one or more guide RNAs or DNA encoding the guide RNAs, wherein the guide RNA leads the endonuclease to a targeted site in the chromosomal sequence and the RNA-guided endonuclease cleaves at least one strand of the chromosomal sequence at the targeted site. The target site can contain or be next to a mutation, e.g., point mutation, a translocation or an inversion which may cause or is associated with a disorder. To correct such a mutation, in some embodiments, the method further comprises contacting or introducing into the cell or embryo at least one donor polynucleotide comprising a wild type counterpart of the mutation and at least one sequence having substantial sequence identity with sequence on one side of the targeted site in the chromosomal sequence.

In one aspect, the method and guide RNA described above can be used for modifying a mammalian cell, including but not limited to in primary cells, stem cells, immortalized cells, and conditionally immortalized cells. Among the phenotypes of cells suitable for the present method and guide RNA are chondrocytes, diabetic cells, epithelial cells, fibroblasts, gastrointestinal cells, hematopoietic stem/progenitor and immune cells, hepatocytes, keratinocytes, melanocytes, neural cells, progenitor cells, renal cells, skeletal muscle cells, smooth muscle cells, sertoli cells, and others.

EXEMPLARY EMBODIMENTS

Exemplary embodiments provided in accordance with the presently disclosed subject matter include, but are not limited to, the following:

1. An isolated guide RNA comprising a guide sequence and a blocking sequence. The guide sequence is capable of hybridizing to a target sequence, and the blocking sequence is capable of hybridizing to at least a portion of the guide sequence.

2. The guide RNA of embodiment 1, comprising a linker between the guide sequence and the blocking sequence.

3. The guide RNA of embodiment 1 or 2, wherein the guide sequence is 12-25 nucleotides long. That is, the guide sequence can be 12, 13, 14, 15, 16, 17, 18, 19, 20, 21, 22, 23, 24 or 25 nucleotides long.

4. The guide RNA of any of embodiments 1-3, wherein the guide sequence is 17-20 nucleotides long.

5. The guide RNA of any of embodiments 1-4, wherein the blocking sequence is 5-20 nucleotides long. That is, the blocking sequence can be 5, 6, 7, 8, 9, 10, 11, 12, 13, 14, 15, 16, 17, 18, 19, or 20 nucleotides long.

6. The guide RNA of any of embodiments 1-5, wherein the blocking sequence is 6-15 nucleotides long.

7. The guide RNA of any of embodiments 1-6, wherein the blocking sequence is 7-12 nucleotides long.

8. The guide RNA of any of embodiments 1-7, further comprising a region with tracrRNA activities.

9. The guide RNA of any one of embodiments 1-8, wherein the guide sequence, the blocking sequence, or both include one or more modified nucleotides.

10. The guide RNA of any one of embodiments 2-9, wherein the linker is 4-20 nucleotides long. That is, the linker can be 4, 5, 6, 7, 8, 9, 10, 11, 12, 13, 14, 15, 16, 17, 18, 19, or 20 nucleotides long.

11. The guide RNA of any one of embodiments 2-10, wherein the linker includes one or more modified nucleotides.

12. The guide RNA of any one of embodiments 2-11, wherein the linker includes one or more selected from the group consisting of a hexadenediol spacer, a TEG spacer, a C3 spacer, and a polyA spacer.

13. The guide RNA of any one of embodiments 1-12, wherein said portion is a 5' portion, a middle portion, or a 3' portion of the guide sequence.

14. A set of RNA molecules comprising two RNAs, one being the guide RNA of any one of embodiments 1-7 and 9-13, and the other being a tracrRNA.

15. A collection or library comprising two or more of the guide RNA of any one of embodiments 1-13, or two or more of the set of embodiment 14.

16. A kit comprising a CRISPR protein or a nucleic acid encoding the CRISPR protein and (i) a guide RNA of any one of embodiments 1-13, or (ii) a set of RNA molecules of embodiment 14, or a collection or library of embodiment 15.

17. A vector encoding the guide RNA of any one of embodiments 1-13, or the set of RNA molecules of embodiment 14.

18. The vector of embodiment 17, further encoding a CRISPR protein.

19. A method for cutting a target nucleic acid with a CRISPR protein or for binding a target nucleic acid with a CRISPR protein, comprising contacting the target nucleic acid with a CRISPR protein and (i) a guide RNA of any one of embodiments 1-13 or (ii) the set of RNA molecules of embodiment 14, to result in a double-strand break or a single-strand break in the target nucleic acid or to result in binding of the target nucleic acid by the CRISPR protein.

20. The method of embodiment 19, wherein the target nucleic acid is located in vivo.

21. The method of embodiment 19, wherein the target nucleic acid is located in vitro.

22. The method of any one of embodiments 19-21, wherein the target nucleic acid is located in a cell or embryo, and the method comprises introducing a nucleic acid that expresses the CRISPR protein into the cell or embryo.

23. The method of any one of embodiments 19-21, wherein the CRISPR protein is contacted with the guide RNA or the set of RNA molecules before being contacted with the target nucleic acid.

24. The method of any one of embodiments 19-23, wherein the method further comprises purifying or partially purifying the pre-complexed CRISPR protein and RNA molecules before contacting the latter to the target nucleic acid.

25. The method of embodiment 22, wherein the target nucleic acid is located in a cell or embryo, and the method comprises introducing a vector that expresses the CRISPR protein and the guide RNA into the cell or embryo.

26. The method of any one of embodiments 19-25, wherein the target nucleic acid is a genomic DNA of a microorganism or a cell of a subject.

27. The method of embodiment 26, wherein the target nucleic acid contains a mutation of the subject.

28. The method of embodiment 26, wherein the subject is an animal or a plant.

29. The method of embodiment 28, wherein the animal is a human.

30. The method of embodiment 26, wherein the microorganism is selected from the group consisting of a virus, a bacterium, and a fungus.

31. The kit of embodiment 16, the vector of embodiment 18, or the method of any one of embodiments 19-30, wherein the CRISPR protein is a type II CRISPR protein.

32. The kit, vector, or method of embodiment 31, wherein the type II CRISPR protein is a Cas9 protein.

33. The kit, vector, or method of embodiment 31 or 32, wherein the CRISPR protein is at least 50% identical to a wild type *S. pyogenes* Cas9 protein (SEQ ID NO:1).

34. The kit, vector, or method of any of embodiments 31-33, wherein the CRISPR protein comprises the sequence of SEQ ID NO:1.

The foregoing description of exemplary or preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. A guide RNA comprising an RNA molecule or a group of RNA molecules, wherein the guide RNA comprises:
   a guide sequence complementary to a target site,
   a protein-binding sequence with tracrRNA activity, and
   a blocking sequence,
   wherein the guide sequence is linked to the blocking sequence, optionally by a linker, wherein the guide sequence is complementary to a target sequence, and the blocking sequence is complementary to at least a portion of the guide sequence such that the blocking sequence competes with the target site and an off-target site for hybridization to the guide sequence, and wherein:
   (i) hybridization of the guide sequence to the target site is thermodynamically favored over competing hybridization of the guide sequence to the blocking sequence, and
   (ii) hybridization of the guide sequence to the blocking sequence is thermodynamically, favored over competing hybridization of the guide sequence to the off-target site.

2. The guide RNA of claim 1, comprising a linker between the guide sequence and the blocking sequence.

3. The guide RNA of claim 1, wherein the guide sequence is 12-25 nucleotides long.

4. The guide RNA of any of claim 1, wherein the blocking sequence is 5-20 nucleotides lone.

5. The guide RNA of claim 1, wherein the guide RNA is a single-guide RNA comprising the guide sequence and the region with tracrRNA activities.

6. The guide RNA of claim 1, wherein the guide sequence, the blocking sequence, or both include one or more modified nucleotides.

7. The guide RNA of claim 2, wherein the linker is 4-20 nucleotides long.

8. The guide RNA of claim 2, wherein the linker includes one or modified nucleotides.

9. The guide RNA of claim 2, wherein the linker includes one or more spacers selected from the group consisting of a hexanediol spacer, a TEG spacer, a 3-amino-1-propanol (C3) spacer, and a polyA spacer.

10. The guide RNA of claim 1, wherein said portion of the guide sequence is a 5' portion, a middle portion, or a 3' portion.

11. A kit comprising a CRISPR protein or a nucleic acid encoding the CRISPR protein and a guide RNA of claim 1.

12. The kit of claim 11, wherein the CRISPR protein is a type II CRISPR protein.

13. A vector encoding the guide RNA of claim 1.

14. The vector of claim 13, further encoding a CRISPR protein.

15. A method for cutting a target nucleic acid with a CRISPR protein or for binding a target nucleic acid with a CRISPR protein, comprising:
   contacting the target nucleic acid with a CRISPR protein and a guide RNA comprising RNA molecule or a group of RNA molecules, wherein the guide RNA comprises:
      a guide sequence complementary to the target nucleic acid,
      a protein-binding sequence having tracrRNA activity, and
      a blocking sequence weakly base-paired with at least a portion of the guide sequence,
      wherein the guide sequence is linked to the blocking sequence, optionally by a linker,
   melting the weakly base-paired blocking sequence from the guide sequence when the blocked guide sequence recognizes the target nucleic acid; and
   hybridizing the target nucleic acid with the guide sequence, wherein the hybridizing of the target nucleic acid is thermodynamically favored over binding of off-target sites, to result in a double-strand break or a single-strand break in the target nucleic acid or to result in binding of the target nucleic acid by the CRISPR protein.

16. The method of claim 15, wherein the target nucleic acid is located in a cell or embryo and the method comprises introducing a nucleic acid that expresses the CRISPR protein into the cell.

17. The method of claim 16, wherein the target nucleic acid is located in a cell or an embryo, and the method comprises introducing a vector that expresses, the CRISPR protein and the guide RNA into the cell or the embryo.

18. The method of claim 15, wherein the target nucleic acid is a genomic DNA of a microorganism or a cell of a subject.

19. The method of claim 15, wherein the CRISPR protein is a type II CRISPR protein.

\* \* \* \* \*

UNITED STATES PATENT AND TRADEMARK OFFICE
CERTIFICATE OF CORRECTION

PATENT NO. : 9,932,566 B2  
APPLICATION NO. : 14/820521  
DATED : April 3, 2018  
INVENTOR(S) : Andrew Kennedy et al.

Page 1 of 1

It is certified that error appears in the above-identified patent and that said Letters Patent is hereby corrected as shown below:

In the Specification

In Column 14, Line 33, delete "spumigenci," and insert -- spumigena, --, therefor.

In the Claims

In Column 33, Line 28, in Claim 1, delete "thermodynamically," and insert -- thermodynamically --, therefor.

In Column 33, Line 36, in Claim 4, delete "lone." and insert -- long. --, therefor.

In Column 33, Line 45, in Claim 8, after "one or" insert -- more --.

In Column 34, Line 46, in Claim 17, delete "expresses," and insert -- expresses --, therefor.

Signed and Sealed this  
Ninth Day of October, 2018

Andrei Iancu  
*Director of the United States Patent and Trademark Office*